United States Patent [19]

Feldstein et al.

[11] 4,154,228

[45] May 15, 1979

[54] APPARATUS AND METHOD OF INSERTING A MICROELECTRODE IN BODY TISSUE OR THE LIKE USING VIBRATION MEANS

[75] Inventors: Cyril Feldstein, Sierra Madre; Donald W. Crawford, Long Beach; Evangelyn W. Kanabus, South Pasadena, all of Calif.

[73] Assignee: California Institute of Technology, Pasadena, Calif.

[21] Appl. No.: 712,270

[22] Filed: Aug. 6, 1976

[51] Int. Cl.² ............................................... A61B 5/00
[52] U.S. Cl. .................................. 128/329 R; 128/639
[58] Field of Search .......... 128/2 E, 2 L, 2 M, 329 R, 128/2.1 E, 2 B, 305, 303 R, 24 A, 1 R, 173 H, 328, 355; 30/272 R, 272 A; 179/100.4 C; 81/9.22

[56] References Cited

U.S. PATENT DOCUMENTS

| 1,713,039 | 5/1929 | Espenshied .................... 179/100.4 C |
| 2,666,651 | 1/1954 | Jones ............................. 179/100.4 C |
| 3,086,288 | 4/1963 | Balamuth et al. ............... 128/305 X |
| 3,569,636 | 3/1971 | Schuller ....................... 179/100.4 C X |
| 3,785,382 | 1/1974 | Schmidt-Kloiber et al. ........ 128/328 |
| 3,826,244 | 7/1974 | Salcman et al. ................. 128/2.1 E |

Primary Examiner—Dalton L. Truluck
Assistant Examiner—Michael H. Thaler
Attorney, Agent, or Firm—Freilich, Hornbaker, Wasserman, Rosen & Fernandez

[57] ABSTRACT

An arrangement for and method of inserting a glass microelectrode having a tip in the micron range into body tissue is disclosed. The arrangement includes a microelectrode. The top of the microelectrode is attached to the diaphragm center of a first speaker. The microelectrode tip is brought into contact with the tissue by controlling a micromanipulator. Thereafter, an audio signal is applied to the speaker to cause the microelectrode to vibrate and thereby pierce the tissue surface without breaking the microelectrode tip. Thereafter, the tip is inserted into the tissue to the desired depth by operating the micromanipulator with the microelectrode in a vibratory or non-vibratory state. A mechanism including a second speaker disclosed. Such mechanism is useful to sense tissue motion to control the microelectrode position with respect thereto substantially constant.

11 Claims, 3 Drawing Figures

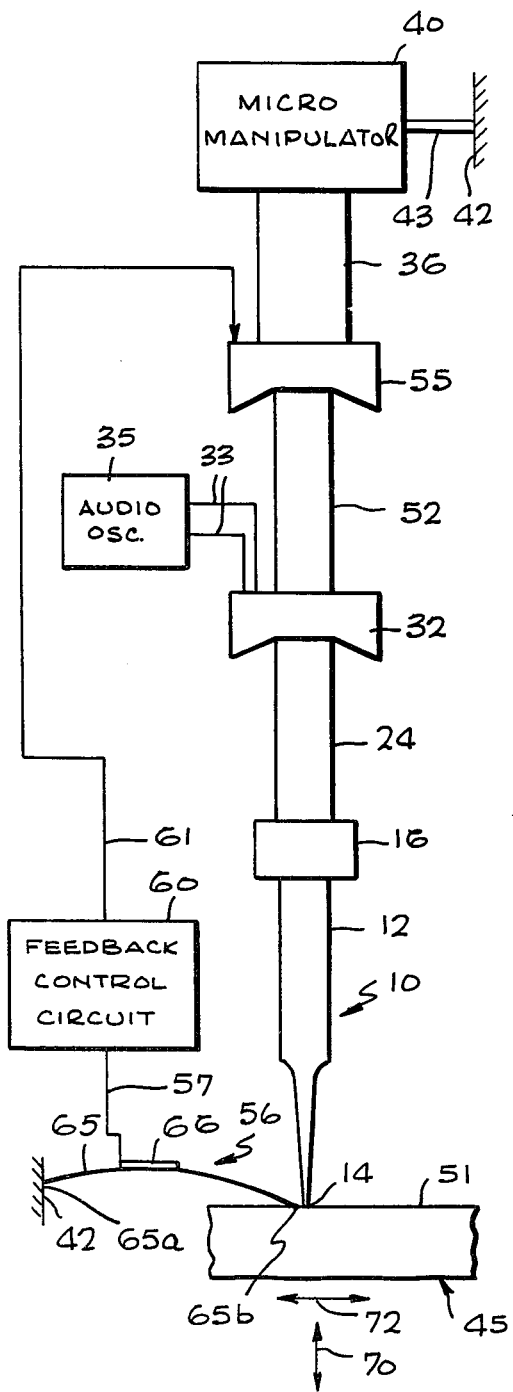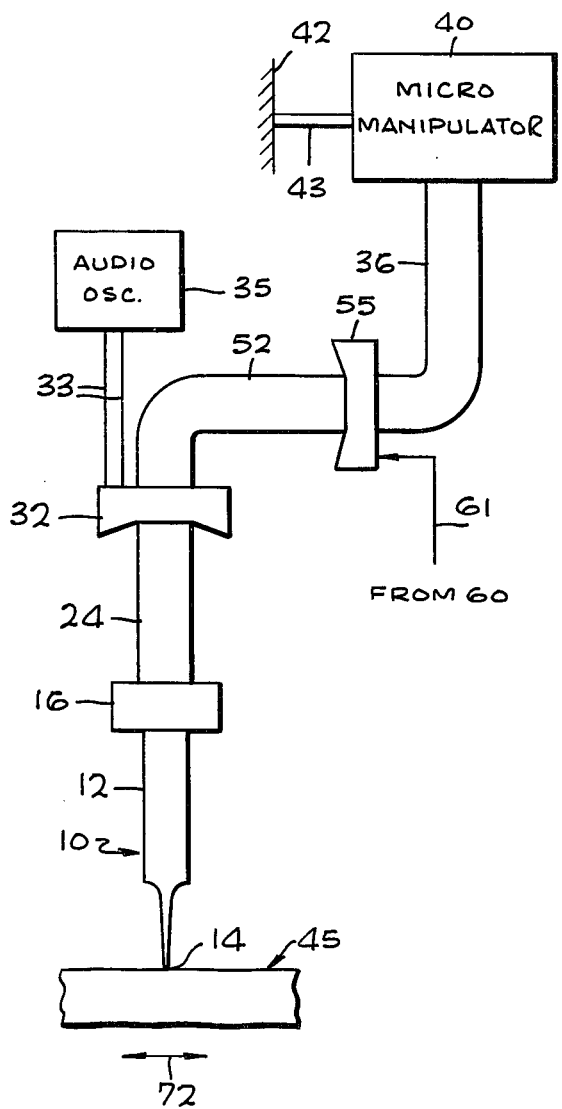

APPARATUS AND METHOD OF INSERTING A MICROELECTRODE IN BODY TISSUE OR THE LIKE USING VIBRATION MEANS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention generally relates to medical instrumentation and, more particularly, to a system for and method of inserting a device into and/or through body tissue.

2. Description of the Prior Art

The present invention will be described in connection with a microelectrode of the type which is insertable into the blood stream in an artery or into the artery wall at a precisely controlled radial distance. However, as will become apparent from the following description, the invention may be used to insert any appropriate medical device into and/or through body tissue, as well as for other purposes, as will be described hereinafter.

The lack of oxygen within the tissue of the internal wall of an artery is in part believed to be one of the possible causes or contributing factors in the development of atherosclerosis. One phase of research in the field of atheroscloerosis is a series of studies to measure the oxygen content (or oxygen potential pressure) in the artery wall at selected radial distance from the artery center, through which blood flows, as well as within the blood stream. Typically, a reference electrode is inserted into the blood stream at any location and at a spaced-apart location an oxygen electrode is inserted, either in the artery wall or in the blood stream. Researchers recognized the fact that for optimum results the electrode should be made as small as possible so as not to affect the blood flow and/or the content of the oxygen in the artery wall to be measured.

During earlier phases of the research in this field metallic hypodermic needles of very small diameters, e.g. 1-2 microns ($\mu$m) were used in fabricating the oxygen electrodes. It was soon discovered that such electrodes were not easily calibrateable and therefore the study results could not be properly interpreted. The primary reason for the difficulty of calibrating such an electrode, is the presence of protein on the metallic needle and the artery outer surface. The electrode interferes with the measurement of oxygen and therefore sets up its own diffusion field, making accurate accumulation of data most difficult.

To overcome this problem an oxygen microelectrode, formed from a glass capillary tube, drawn out to form a long tapering point, with a tip of 1-2$\mu$m was developed. Such a microelectrode, hereinafter referred to as the glass microelectrode, is described in an article entitled "A Microelectrode for Measuring Intercellular PO$_2$" by W. J. Whalen et al published in J. Appl. Physiol. 23 (5) 798-801, 1967. The glass microelectrode, unlike the electrode with the metallic hypodermic needle, overcomes the calibration problem. However, as pointed out in the article, and as experienced by researchers, who use such a glass microelectrode, the principal disadvantage of the glass microelectrode is its fragility. The glass microelectrode, which is difficult to make and therefore quite costly, tends to break when attempting to pierce the artery wall therewith. Furthermore, even when the glass microelectrode is successfully inserted into the artery wall, quite often the force used during artery piercing and electrode insertion, tends to deform the artery by forming a dimple therein at the point where the electrode is pressed against the artery, which disturbs the oxygen profile across the artery wall. This is most undesirable.

A need therefore exists for a system or arrangement and method with which a glass microelectrode may be safely inserted into an artery wall, without breaking the microelectrode and/or without disturbing the oxygen profile in the artery wall. A need also exists for a system and method for inserting any medical device, e.g., a transducer, into relatively hard or thick tissue, e.g., a heart muscle, at a desired depth with a minimum of force so as not to disturb and/or injure the tissue.

OBJECTS AND SUMMARY OF THE INVENTION

It is a primary object of the present invention to provide a system for the insertion of a device into body tissue with a minimum of effect on the tissue.

Another object of the invention is to provide a system for and/or a method of inserting a highly fragile glass microelectrode into body tissue to a controlled depth without electrode breakage.

A further object is to provide a system for and/or a method of inserting a microelectrode into body tissue with a minimum of force on the tissue so as to minimize any adverse effects thereon.

Yet another object is to provide a system for and/or method of inserting a medical device into body tissue to a controlled depth with a minimum of force so as not to deform the tissue and without endangering the inserted medical device.

These and other objects of the invention are achieved by providing a system whereby the medical device, e.g., the glass microelectrode is first positioned against the tissue to be inserted. Means are provided to vibrate the glass microelectrode at a selected rate, so that as it vibrates it pierces the tissue and thereafter is inserted into the tissue of a desired depth. The microelectrode may be vibrated as it is positioned within the tissue to the desired depth. In one embodiment the vibration of the microelectrode is achieved by attaching the electrode to the diaphragm of a microspeaker which is energized with a signal in the audio range. The back and forth vibrations of the diaphragm are transmitted to the microelectrode, causing it to vibrate along its longitudinal axis. In preferred embodiment means, including a second speaker, are employed to maintain the electrode at the desired position within the artery, irrespective of movements of the latter.

The novel features of the invention are set forth with particularity in the appended claims. The invention will best be understood from the following description when read in conjunction with the accompanying drawings.

BRIEF DESCRIPTION OF THE DRAWINGS

FIGS. 2 and 3 are block diagrams of two other embodiments of the invention.

DESCRIPTION OF THE PREFERRED EMBODIMENTS

Figure 1:
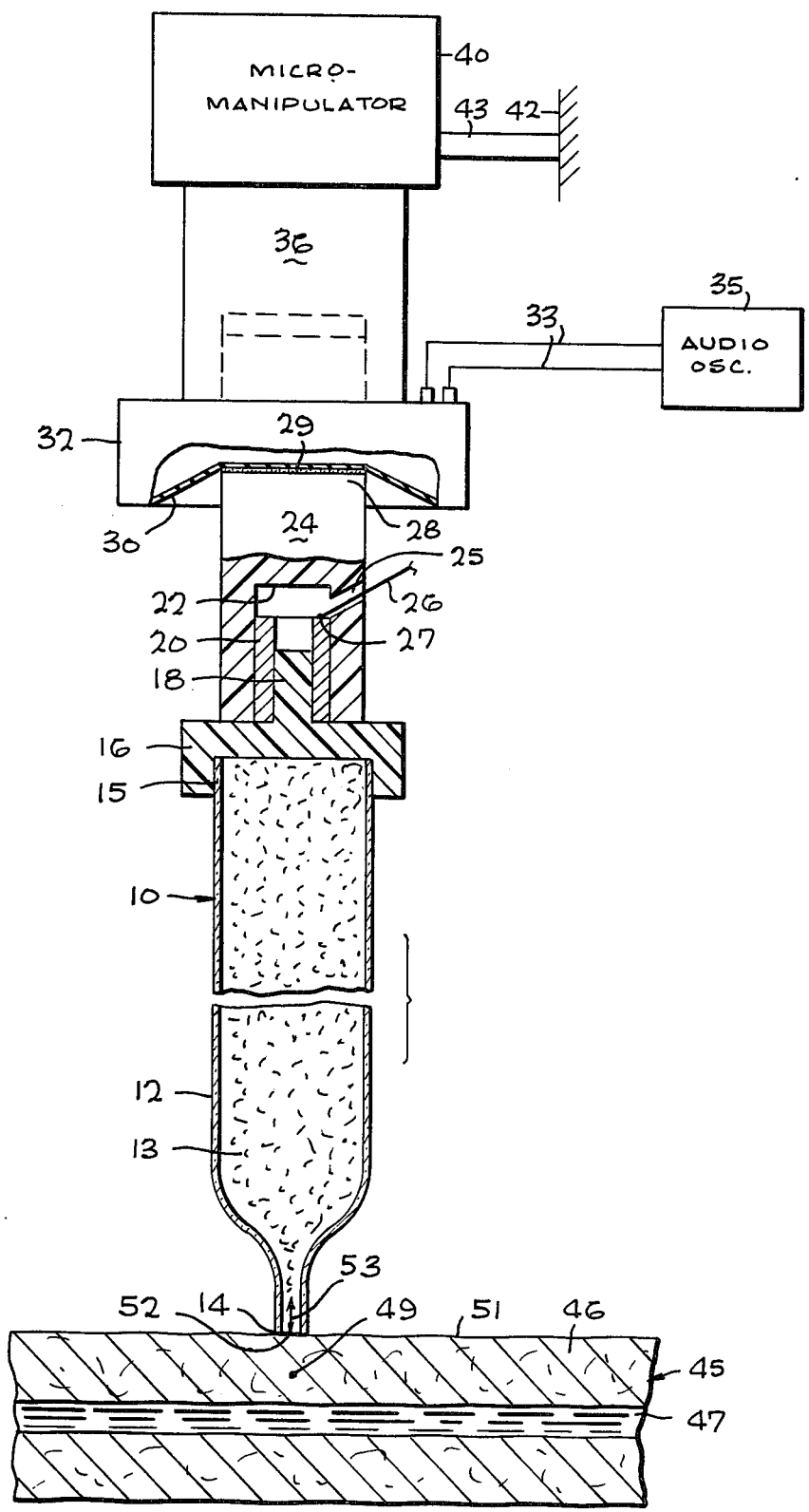
FIG. 1 is a combination block and sectional view of one embodiment of the invention.

The basic principles of the present invention may best be described by directing attention to the embodiment, shown in FIG. 1, wherein numeral 10 generally designates an oxygen glass microelectrode. Typically, it is formed of a glass capillary tube 12, drawn so as to form a long tapering point with a tip 14 on the order of 1–2 microns ($\mu$m) in diameter. The tube 12 is assumed to be filled with appropriate matter 13, such as Woods metal which fills the tube almost to its tip 14. Since the actual construction of the oxygen glass microelectrode does not form part of the invention and is well known, the oxygen glass microelectrode 10 will not be described in further detail. The tube 12 at its end 15, opposite tip 14 is held by a collar-like holder 16 from which a stud-like member, hereinafter referred to as stud 18, extends. Holder 16 with its stud 18 are formed of an electrically conductive metal, e.g., brass, which is in contact with the electrically conductive matter 13 which fills the tube 12.

The stud 18, which is typically axially aligned along the longitudinal axis of tube 12 of the microelectrode 10, is a pressure fit within a metallic bushing 20, located in an opening 22 of a support rod 24. The latter, which may be formed of a hard plastic material and is generally electrically non-conductive, defines an opening 25 through which an electrode lead 26 extends and is in electrical contact at one of its ends with the bushing 22, as shown at 27. Lead 26 is assumed to be connected at its other end to an appropriate recording or measuring device. Lead 26 is effectively in electrical contact with matter 13 filling the tube 12 through the bushing 20, stud 18 and holder 16.

End 28 of the support rod 24, which is opposite the end through which the stud 18 is inserted into bushing 20 is permanently secured, such as by glue 29, to the diaphragm 30 of a small speaker 32. The latter is assumed to be connected by means of lead 33 to an audio oscillator 35. The function of the latter is to provide an audio signal to the speaker 32 and thereby cause its diaphragm 30 to vibrate, which in turn causes the support rod 24 and any of the parts connected thereto such as the microelectrode 10 to vibrate.

As is appreciated the diaphragm vibrates back and forth along its central axis. Thus, as the diaphragm vibrates it causes the microelectrode 10 with its very small tip 14 to vibrate back and foth along the microelectrode longitudinal axis. The vibration stroke is related to the frequency of the audio signal which is applied to the speaker 32 from oscillator 35. In one embodiment actually reduced to practice an audio frequency of about 200 Hz was found to provide satisfactory vibration to a glass microelectrode by means of a commercially available microspeaker. It should be apparent that the invention is not intended to be limited to the use of an audio signal in the range of about 200 Hz, which is mentioned herein as an example rather than to limit the invention thereto.

The speaker 32 is shown connected at its back end to a rod 36 which extends from a micromanipulator 40, shown attached to a reference position 42 such as by means of a linkage arm 43. The function of the micromanipulator 40 is to raise and lower the rod 36 extending therefrom and thereby control the position of tip 14 of the microelectrode 10, which is physically connected to rod 36 through rod 24 and speaker 32. In one embodiment rods 36 and 24 were formed of lucite material.

In the absence of an audio signal from audio oscillator 35 the diaphragm 30 is stationary therefore the position of the electrode tip 14 is directly controlled by the micromanipulator 40. At any tip position, controlled by manipulator 40, when an audio signal from oscillator 35 is applied to speaker 32 its diaphragm 35 vibrates back and forth. Thus, as the diaphragm 30 vibrates, it causes the glass microelectrode 10 with its tip 14 to vibrate along its longitudinal axis.

As previously explained, the glass microelectrode may be used to measure the oxygen content in the blood stream or at selected depths in the wall of an artery. The outer artery surface may be used as the reference surface in controlling the distance or depth in the artery wall at which the tip 14 is to be located. In FIG. 1, numeral 45 designates the artery, while numeral 46 designates the artery wall and 47 the stream of blood flowing through the artery. As previously indicated, with the novel system of the present invention, the electrode tip 14 can be inserted to any preselected depth in the artery wall 46 for example, as represented by 49 without breaking the electrode tip 14 or any portion thereof adjacent to the tip, and without deforming the artery wall so as to affect the oxygen content thereof.

There are several ways in which this may be accomplished with the novel system of the present invention. One way is to lower the microelectrode 10 with its tip 14 by means of the micromanipulator 40 until the tip 14 touches the outer surface 51 of the artery wall 46. Thereafter, the audio signal is applied to the speaker 32 by audio oscillator 35. Consequently, the electrode tip 14 vibrates back and forth thereby piercing the surface 51 of the artery 45 at point 52. The tip vibration is represented by double-headed arrow 53. Once the artery surface 51 is pierced, the tip 14 is inserted into the wall at a desired depth, for example point 49, by operating the micromanipulator 40 to lower the microelectrode 10 toward the artery. If desired, during insertion of the tip into the artery wall the tip may be continually vibrated by the continuous application of the audio signal. On the other hand, once the artery wall piercing takes place by the vibrating microelectrode, its vibration may be terminated by terminating the supply of the audio signal to the speaker 32. Thereafter, the tip may be located at the desired position by lowering the microelectrode by means of micromanipulator 40, with the microelectrode being in a non-vibratory state.

It has been discovered that with the system hereinbefore described, the glass microelectrode 10 is practically immune to breakage and that practically no artery deformation takes place during the microelectrode insertion. This is realized since with the present invention the piercing of the artery is not achieved by applying a reasonably large force to the very fragile electrode tip which when it does not break, tends to significantly deform the artery wall by forming a large dimple therein at the point at which the electrode is pressed against the artery, but rather artery piercing is achieved by the vibrating electrode tip which vibrates at a selected frequency in the audio range so that minimal force, if any, is needed to pierce the artery surface. In one embodiment an audio frequency of about 200 Hz was found to be quite advantageous. Once piercing of the artery wall takes place, the electrode tip may be inserted into the desired depth with the electrode either in the vibratory or non-vibratory state.

The teachings of the invention have been practiced very successfully with a glass microelectrode which in one embodiment consisting of a glass capillary tube with approximately 1 mm outside diameter (OD) and an inner diameter (ID) of about 0.25 mm, which was drawn to form an elongated tapered end of about 6–9 mm long along the longitudinal axis of the tube, and terminating in a tip 14 of about 1–2 microns in diameter. The speaker which was used in the particular embodiment comprised a miniature speaker of 1.5 inches in diameter, which is commercially available from GE Electronics, Division of Hydrometals Inc., Rockford, Illinois 61101, as Model No. S2-0215.

As previously pointed out, in the prior art method of microelectrode insertion, due to the extremely small diameter (1–2μm) of the tip 14 of the glass microelectrode, very often the tip breaks, when an operator attempts to pierce the artery wall within the small microelectrode tip. The outer surface of an artery is relatively dense. Consequently, a relatively large force has to be used to pierce the artery wall. Typically, the microelectrode is inserted by pushing or pressing the tip against the artery wall until the artery surface is pierced. Very often even with the minimum pressure needed to pierce the artery, the tip breaks. Furthermore, even when the tip does not break the force which is applied causes the artery to be deformed by forming a relatively large dimple at and around the point of contact between the tip and the artery surface. This is quite undesirable since large artery dimpling may affect the oxygen content profile across the artery wall.

These problems are practically eliminated with the present invention in which artery piercing is achieved with the microelectrode tip while the tip vibrates back and forth along its longitudinal axis. When the tip vibrates the force needed to pierce the artery is minimal and therefore the counter force which the artery applies to the tip is extremely small. Consequently, the tip does not break, which is a major advantage of the invention. Also, due to the vibrating tip, artery piercing is achievable with no visible artery dimpling. Thus, the oxygen content profile in the artery wall is not disturbed.

The force needed to insert the tip at the desired depth is generally less than that needed for piercing since the artery wall itself is softer than its outer surface. Thus, once artery piercing is achieved, the oscillation or vibration of the microelectrode may be terminated. However, if the wall itself is found to be relatively hard, the microelectrode may be vibrated until the tip reaches the desired portion within the artery wall. Since the tip 14 and the portion of the microelectrode which extends back from the tip is of extremely small diameter, the portion of the microelectrode which is inserted into the wall does not affect the oxygen content profile to any significant degree. Thus, accurate measurements of oxygen content can be performed. Glass microelectrodes whose tips broke when attempts were made to insert them in arteries by prior art methods, were subsequently used with great success when practicing the teachings of the present invention.

From the foregoing, it should thus be apparent that in accordance with the present invention means are provided for inserting a glass microelectrode into an artery or other body tissue by causing the glass microelectrode to vibrate along its longitudinal axis, at least during the piercing of the outer surface of the artery. As described, the vibration of the electrode along its longitudinal axis is provided by the vibrations of a diaphragm of an audio speaker, energized by an audio signal from an appropriate source, such as the audio oscillator 35. Except for the vibrating motion of the microelectrode its position and therefore its tip portion with respect to the stationary reference position 42 is controlled by the micromanipulator 40. With the embodiment shown in FIG. 1, the tip position resolution depends on the position resolution of the micromanipulator which may be on the order of 2 microns. With the embodiment shown in FIG. 1 the depth of tip insertion into a stationary artery wall is easily controlled by first lowering the tip to come in contact with the artery surface 51 and after artery piercing lowering the tip by means of micromanipulator 40 to the desired depth with respect to the artery surface.

However, such an insertion technique may not be sufficiently satisfactory if the artery, rather than being at rest or stationary moves with respect to the micromanipulator 40. e.g., up and down. Successful insertion of the microelectrode 10 into a moving artery is achievable with an arrangement as shown in FIG. 2, wherein elements like those previously described are designated by like numerals.

In the embodiment shown in FIG. 2 the microspeaker 32 rather than being connected directly to rod 36 of the micromanipulator 40 is connected to a rod 52. The latter is permanently secured such as by glue to the center of the diaphragm of a second speaker 55 which is connected to rod 36 of micromanipulator 40.

Also included are means 56 used to sense the motion such as up and down of the artery 45 with respect to the fixed reference position 42 and to supply via a line 57 a feedback signal related to the artery motion with respect to position 42 to a feedback control circuit 60. The latter supplies a signal via line 61 to the second speaker 55 causing the diaphragm of the latter to move up and down as in synchronism with the up and down motion of the artery 45. Consequently, the distance between tip 14 and artery surface 51 is held substantially constant. That is, as far as the microelectrode the artery distance therefrom is constant as if the artery were at rest. Once this distance is held constant the tip is lowered to the artery surface 51 by micromanipulator 40, and thereafter the microspeaker 32 is activated to cause the vibration of the microelectrode 10 to pierce the artery as hereinbefore described.

It should be apparent that various arrangements may be used in implementing means 56 to provide a signal related to the motion or position of the artery surface 51 with respect to the fixed reference position 42. For example, the means 56 may comprise a curved beam 65 of high elastic compliance having an end 65a secured to the reference position 42 and another end 65b in contact with the artery surface 51 near the point where the surface is to be pierced. The up and down motion of the artery surface 51 varies the curvature of beam 64, which may be sensed by a strain gauge 56, whose output is the feedback signal supplied to control circuit 60.

In the arrangement shown in FIG. 2 the center of the second speaker 55 is shown aligned with the longitudinal axis of the microelectrode 10. Such an arrangement is desirable if the artery 45 moves up and down in the direction or axis in which the tip 14 is to be inserted, as represented by double-headed arrow 70. If, however, the artery moves sideways with respect to the microelectrode longitudinal axis, such as represented by arrows 72 in FIGS. 2 and 3 the second speaker 55 may be oriented with an axis along its counter perpendicular to the microelectrode's longitudinal axis, as shown in FIG. 3. In such an arrangement the feedback signal to the control circuit 60 may be provided from a miniature displacement transducer, for example a transducer like the one described in U.S. Pat. No. 3,937,212.

It should be stressed that although hereinbefore the invention has been described in connection with inserting a glass microelectrode into body tissue such as an artery it is not intended to be limited thereto. The invention in which vibrating means, such as the microspeaker 32, is used to vibrate the microelectrode may be used to vibrate any medical device to facilitate its insertion into selected body tissue.

For example, the novel system of the present invention may be used to insert a subminiature force transducer such as the one described in U.S. Pat. No. 3,905,356 into selected body tissue, e.g., the heart which is a relatively hard muscle. By causing the transducer to vibrate while it is inserted into the heart less force would be needed for its proper insertion since the vibrating transducer would tend to decrease the frictional forces of heart muscle and make it more pliable. One can view the vibrating transducer (or the previously described glass microelectrode) as a microjackhammer in its effect on the tissue which it is intended to pierce and be inserted therein. Also, the location of the transducer in the heart when inserted in accordance with the present invention may be more accurately controlled by means of the micromanipulator 40 than by merely approximating its inserted position.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. In a method of inserting a device in body tissue or the like, the steps comprising:
    providing an audio speaker with a vibratory member which vibrates when an audio signal is applied to said speaker;
    attaching said device to said vibratory member; and
    vibrating said device to pierce the tissue outer surface by applying an audio signal to said speaker.

2. The method as described in claim 1 further including the step of inserting said device into said tissue to a selected depth from said outer surface after said outer surface has been pierced.

3. The method as described in claim 2 wherein said device is vibrated while it is inserted into said tissue.

4. The method as described in claim 1 further including the step of inserting said device into said tissue to a selected depth from said outer surface after said outer surface has been pierced, and wherein said device is vibrated while it is inserted into said tissue.

5. The method as described in claim 1 wherein said body tissue is nonstationary and the method further includes the steps of sensing the motion of said body tissue and controlling the device position with respect to said tissue as a function of the sensed motion of said tissue.

6. The method as described in claim 1 wherein said device is controllably movable toward and away from said tissue with respect to a fixed reference position and said tissue is in a nonstationary state, the method including the steps of sensing changes in the position of said tissue with respect to said reference position and controlling the device position as a function of the changes in the position of said tissue.

7. An arrangement for inserting a device into body tissue or the like comprising:
    an elongated device of the type defining a front end adapted to be inserted into body tissue or the like;
    support means connected to said device at an end other than said front end, said support means including energizable means comprising a first audio speaker with a vibratory member, which vibrates back and forth along an axis when said speaker is energized by an energizing signal;
    mechanical means for mechanically rigidly connecting said vibratory member to said devices, with the front end thereof along said axis, whereby when said vibratory member vibrates along said axis, said front end of said device vibrates therewith along said axis;
    energizing means for selectively energizing said speaker; and
    positioning means coupled to said support means for controlling the position of said device with the front end thereof with respect to the tissue into which said device is adapted to be inserted, said positioning means include means adapted to sense the motion of said tissue and control means for varying the position of the support means as a function of the sensed tissue motion, said control means comprises a second audio speaker, having a vibratory diaphragm connected to said support means, and a circuit means for applying a signal to said second speaker as a function of the sensed tissue motion so as to cause the diaphragm of said second speaker to move in a direction to thereby control the distance between said support means and said moving tissue substantially constant, when the position of the device with respect to said tissue is not varied by said energizing means.

8. The arrangement as described in claim 7 wherein the centers of the diaphragms of both speakers are aligned along the longitudinal axis of said device with which said device first end is aligned.

9. An arrangement for inserting a device into body tissue or the like, comprising:
    an elongated device of the type defining a front end, adapted to be inserted into body tissue or the like;
    support means connected to said device at an end other than said front end, said support means including energizable means comprising a vibratory member which vibrates so as to cause said device to vibrate along an axis with which said device's front end is aligned, upon the application of an energizing signal to said energizable means;
    energizing means for selectively energizing said energizable means; and
    positioning means, coupled to said support means, for controlling the position of said device with the front end thereof with respect to the tissue into which said device is to be inserted, said positioning means include means adapted to sense motion of said tissue and control means for varying the position of the support means as a function of the sensed tissue motion, said energizable means comprising a first audio speaker, and said vibratory member is the speaker's diaphragm and said energizing means is a source of audio signals for energizing said first speaker, and said control means comprises a second audio speaker having a vibratory diaphragm connected to said support means, and circuit means for applying a signal to said second speaker as a function of the second tissue motion so as to cause the diaphragm of said second speaker to move in a direction to thereby control the distance between the support means and said moving tissue substantially constant, when the position of the device with respect to said tissue is not varied by said energizing means.

10. The arrangement as described in claim 9 wherein the centers of the diaphragms of both speakers are aligned along the longitudinal axis of said device with which said device first end is aligned.

11. The arrangement as described in claim 10 wherein said device is a microelectrode comprising an elongated tube with a tapered end terminating in a tip defining the device's first end.